(12) United States Patent
Im et al.

(10) Patent No.: US 12,288,479 B2
(45) Date of Patent: Apr. 29, 2025

(54) VOICE SELF-TRAINING METHOD AND USER TERMINAL DEVICE FOR VOICE IMPAIRED PATIENT

(71) Applicant: THE CATHOLIC UNIVERSITY OF KOREA INDUSTRY-ACADEMIC COOPERATION FOUNDATION, Seoul (KR)

(72) Inventors: Sun Im, Seoul (KR); Cheol Ki Kim, Seoul (KR)

(73) Assignee: THE CATHOLIC UNIVERSITY OF KOREA INDUSTRY ACADEMIC COOPERATION FOUNDATION, Seoul (KR)

( * ) Notice: Subject to any disclaimer, the term of this patent is extended or adjusted under 35 U.S.C. 154(b) by 28 days.

(21) Appl. No.: 18/251,840

(22) PCT Filed: Oct. 22, 2021

(86) PCT No.: PCT/KR2021/014866
§ 371 (c)(1),
(2) Date: May 4, 2023

(87) PCT Pub. No.: WO2022/154217
PCT Pub. Date: Jul. 21, 2022

(65) Prior Publication Data
US 2024/0021096 A1    Jan. 18, 2024

(30) Foreign Application Priority Data

Jan. 14, 2021  (KR) .................. 10-2021-0005571

(51) Int. Cl.
*G09B 5/02*    (2006.01)
*A61B 5/00*    (2006.01)

(52) U.S. Cl.
CPC .............. *G09B 5/02* (2013.01); *A61B 5/4803* (2013.01)

(58) Field of Classification Search
CPC ................................ A61B 5/4803; G09B 5/02
See application file for complete search history.

(56) References Cited

U.S. PATENT DOCUMENTS

2011/0112855 A1    5/2011   Chen

FOREIGN PATENT DOCUMENTS

JP    2003186379 A    7/2003
JP    2020-201810 A   12/2020
(Continued)

OTHER PUBLICATIONS

International Search Report and Written Opinion issued in connection with corresponding PCT Patent Application No. PCT/KR2021/014866 dated Feb. 9, 2022.

*Primary Examiner* — Kesha Frisby
(74) *Attorney, Agent, or Firm* — Tarolli, Sundheim, Covell & Tummino LLP

(57) ABSTRACT

Provided are a self voice training method for a patient with a voice disorder and a user terminal for self voice training. The user terminal for self voice training includes an input device configured to receive a training program selection command of a user, a storage configured to store voice training candidate programs for the user's voice training, a calculator configured to generate first guide content according to a first voice training program selected from among the voice training candidate programs by the user, an output device configured to output the first guide content, and a microphone configured to receive voice output by the user according to the first guide content output through the output device.

15 Claims, 8 Drawing Sheets

(56) References Cited

FOREIGN PATENT DOCUMENTS

| | | | |
|---|---|---|---|
| KR | 1020140128630 | A | 11/2014 |
| KR | 10-2017-0008970 | A | 1/2017 |
| KR | 101921888 | B1 | 11/2018 |

(A)

(B)

(A)

(B)

(A)

(B)

(A)

(B)

ID DEVICE FOR VOICE
VOICE SELF-TRAINING METHOD AND USER TERMINAL DEVICE FOR VOICE IMPAIRED PATIENT

RELATED APPLICATIONS

The present invention is a U.S. National Stage under 35 USC 371 patent application, claiming priority to PCT Application No. PCT/KR2021/014866, filed on Oct. 22, 2021, which claims priority from Korean Patent Application No. 10-2021-0005571 filed on Jan. 14, 2021; the entireties of both are hereby incorporated herein by reference.

BACKGROUND

1. Field

The present invention relates to a device and method for self voice training.

2. Discussion of Related Art

Voice disorders may have various causes. Voices disorders may be divided into organic disorders caused by voice abuse, trauma, inflammation, etc. and functional disorders caused by stress or neurological diseases. There are various ways to treat voice disorders, and voice therapy through vocalization is widely used.

Voice therapy is a method in which medical staff proposes appropriate vocal training to a patient through face-to-face medical treatment. Traditional voice therapy methods are provided by medical staff with specialized knowledge and thus may not be universally available to patients with voice disorders. Also, in the case of self-training, elderly patients have difficulty accurately recognizing their vocalization due to hearing loss.

SUMMARY

The present invention is directed to providing self voice training through a user terminal, such as a smartphone, using information technology (IT).

The present invention is also directed to providing self voice training in which even elderly patients may intuitively discover their vocalization states.

According to an aspect of the present disclosure, there is provided a self voice training method for a patient with a voice disorder, the self voice training method including outputting, by a user terminal, first guide content for voice training on a screen, receiving, by the user terminal, voice output by a user according to the first guide content, analyzing and evaluating, by the user terminal, the voice, outputting, by the user terminal, second guide content according to a result of the evaluation, and receiving, by the user terminal, voice output by the user according to the second guide content.

According to another aspect of the present disclosure, there is provided a self voice training method for a patient with a voice disorder, the self voice training method including outputting, by a user terminal, first guide content for voice training on a screen, receiving, by the user terminal, voice output by a user according to the first guide content, receiving, by the user terminal, an evaluation result of the voice from a diagnoser terminal, outputting, by the user terminal, second guide content according to the evaluation result on the screen, and receiving, by the user terminal, voice output by the user according to the second guide content.

According to another aspect of the present disclosure, there is provided a user terminal for self voice training, the user terminal including an input device configured to receive a training program selection command of a user, a storage configured to store voice training candidate programs for the user's voice training, a calculator configured to generate first guide content according to a first voice training program selected from among the voice training candidate programs by the user, an output device configured to output the first guide content, and a microphone configured to receive voice output by the user according to the first guide content output through the output device. The calculator selects a second voice training program from among the voice training candidate programs according to an evaluation result of the voice of the user and generates second guide content according to the second voice training program, and the output device outputs the second guide content.

The first guide content and the second guide content are data for outputting content of a voice training program as a visual object over time.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
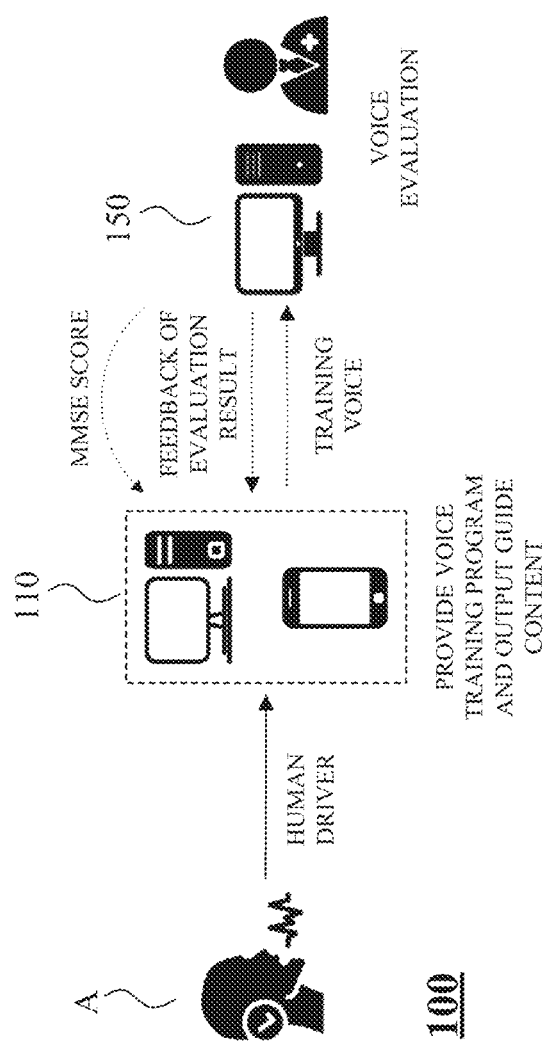
FIG. 1 is a diagram showing an example of a self voice training system.

As the technology described below allows for various modifications and several embodiments, particular embodiments will be illustrated in the drawings and described in detail. However, this is not intended to limit the present invention to particular embodiments, and it is to be understood that all modifications, equivalents, and substitutes within the technical spirit and scope of the technology described below are encompassed in the technology.

Terms such as "first," "second," "A," "B," etc. are used to describe various components, but the components are not limited by the terms. The terms are used only for the purpose of distinguishing one component from another. For example, a first component may be named a second component without departing from the scope of the technology described below, and similarly, a second component may be named a first component. The term "and/or" includes any and all combinations of a plurality of associated listed items.

As used herein, the singular forms are intended to include the plural forms as well unless the context clearly indicates otherwise. It will be understood that the terms "comprises," "includes," etc. specify the presence of stated features, integers, steps, operations, components, parts, or combinations thereof and do not preclude the presence or addition of one or more other features, integers, steps, operations, components, parts, or combinations thereof.

Prior to detailed description of the drawings, it is to be clarified that the classifications of components in the present specification are merely classifications for main functions performed by the components. In other words, two or more components to be described below may be combined into one component, or one component may be subdivided into two or more components for more subdivided functions. Also, each component to be described below may perform some or all functions of other components in addition to its own main function, and some of the main functions of components may be exclusively performed by another component.

In the case of performing a method or operation method, operations of the method may occur in a different order from the specified order unless the context clearly indicates a specific order. In other words, the operations may occur in the same order as specified, occur substantially concurrently, or occur in the reverse order.

The technology described below is a technique for a user to do self voice training using a user terminal. The user terminal is a device that may receive voice, process a voice signal, and output certain information. For example, the user terminal may be a personal computer (PC), a laptop computer, a smartphone, a smart device, a smart watch, a wearable device, a smart television (TV), etc.

FIG. 1 is a diagram showing an example of a self voice training system 100.

A user A is assumed to be a patient with a voice disorder. The user A performs self voice training using a user terminal 110. As examples of the user terminal 110, a PC and a smartphone are shown in FIG. 1.

The user terminal 110 provides a program for voice training (hereinafter, a "voice training program"). The voice training program is a program for various types of self voice training. Here, the program is training content. The user terminal 110 may provide a specific voice training program selected by the user A. The user terminal 110 outputs guide content according to the voice training program. The guide content is information for delivering information such as the length, the pitch, the strength, etc. of sound that the user A is required to vocalize over time to the user A with ease. The guide content will be described in detail below.

The user A may watch the guide content output on the user terminal 110 and vocalize (output) sound suitable for the current point in time. The user terminal 110 receives voice from the user A according to the voice training program. The voice produced by the user A according to the voice training program is referred to as training voice.

The user terminal 110 may transmit the training voice to an evaluator terminal 150. The evaluator terminal 150 evaluates the training voice. The evaluator terminal 150 may output the training voice and receive the evaluator's evaluation result of the output training voice. This is subjective evaluation by the evaluator. The evaluator may be medical staff.

Meanwhile, evaluation of the training voice may be automatically performed. The evaluator terminal 150 may calculate an evaluation result by analyzing the training voice. Various technologies may be used in voice signal analysis. Voice signal analysis may be performed on the basis of features in a frequency band. Voice signal analysis may also be performed using a learning model (a deep learning model or the like).

The evaluation result of the training voice is fed back to the user terminal 110. Further, the user terminal 110 may evaluate the training voice by analyzing the training voice using a voice evaluation model.

Also, the user terminal 110 may receive diagnosis information of the user A from the evaluator terminal 150. In addition, the user terminal 110 may receive the diagnosis information from a separate object having medical information of the user A. For example, the user terminal 110 may receive the diagnosis information from an electronic medical record (EMR) server of a hospital. The diagnosis information may be evaluation information of cognitive functions. The diagnosis information may be a mini-mental state examination (MMSE) score. The diagnosis information is information related to a linguistic disorder of the user A.

The user terminal 110 may select a voice training program to be provided to the user A on the basis of the evaluation result of the training voice. Also, the user terminal 110 may select a voice training program to be provided to the user A on the basis of the evaluation result and diagnosis information of the training voice.

The user terminal 110 may output guide content according to the newly selected voice training program. The user A performs voice training according to the new voice training program.

Figure 2:
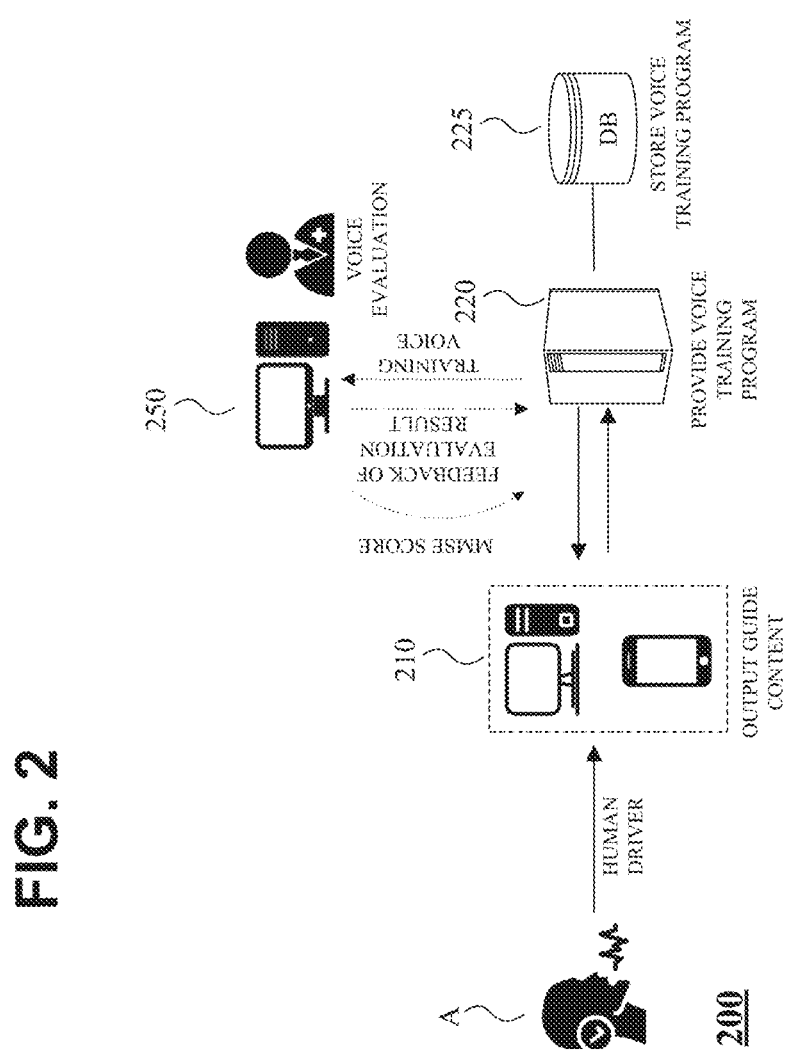
FIG. 2 is a diagram showing another example of a self voice training system.

FIG. 2 is a diagram showing another example of a self voice training system 200. The self voice training system 200 corresponds to a system employing a server for voice training.

A user A is assumed to be a patient with a voice disorder.

A service server 220 provides a voice training program to a user terminal 210. As examples of the user terminal 210, a PC and a smartphone are shown in FIG. 2.

The user terminal 210 outputs guide content according to the voice training program. The guide content is information for delivering information such as the length, the pitch, the strength, etc. of sound that the user A is required to vocalize over time to the user A with ease.

The user A may watch the guide content output in the user terminal 210 and vocalize (output) sound suitable for the current point in time. The user terminal 210 receives training voice from the user A according to the voice training program.

The user terminal 210 may transmit the training voice to a service server 220. The service server 220 may transmit the training voice to an evaluator terminal 250. The evaluator terminal 250 may output the training voice and receive the evaluator's evaluation result of the output training voice. The evaluator may be medical staff.

Meanwhile, evaluation of the training voice may be automatically performed. The evaluator terminal 250 may calculate an evaluation result by analyzing the training voice. Voice signal analysis may be performed on the basis of features in a frequency band. Voice signal analysis may also be performed using a learning model (a deep learning model or the like).

The evaluation result of the training voice is fed back to the service server 220. Further, the service server 220 may evaluate the training voice by analyzing the training voice using a voice evaluation model.

Also, the service server 220 may receive diagnosis information of the user A from the evaluator terminal 250. In addition, the service server 220 may receive the diagnosis information from a separate object having medical information of the user A. For example, the service server 220 may receive the diagnosis information from an EMR server of a hospital. The diagnosis information may be evaluation information of cognitive functions. For example, the diagnosis information may be an MMSE score. The diagnosis information is information related to a linguistic disorder of the user A.

The service server 220 may select a voice training program to be provided to the user A on the basis of the evaluation result of the training voice. A training database (DB) 225 stores a variety of voice training programs. The service server 220 may select a voice training program matching the evaluation result from among the voice training programs in the training DB 225. Also, the service server 220 may select a voice training program to be provided to the user A on the basis of the evaluation result and diagnosis information of the training voice.

The service server 220 transmits a newly selected voice training program to the user terminal 210. The user terminal 210 may output guide content according to the newly selected voice training program. The user A performs voice training according to the new voice training program.

Figure 3:
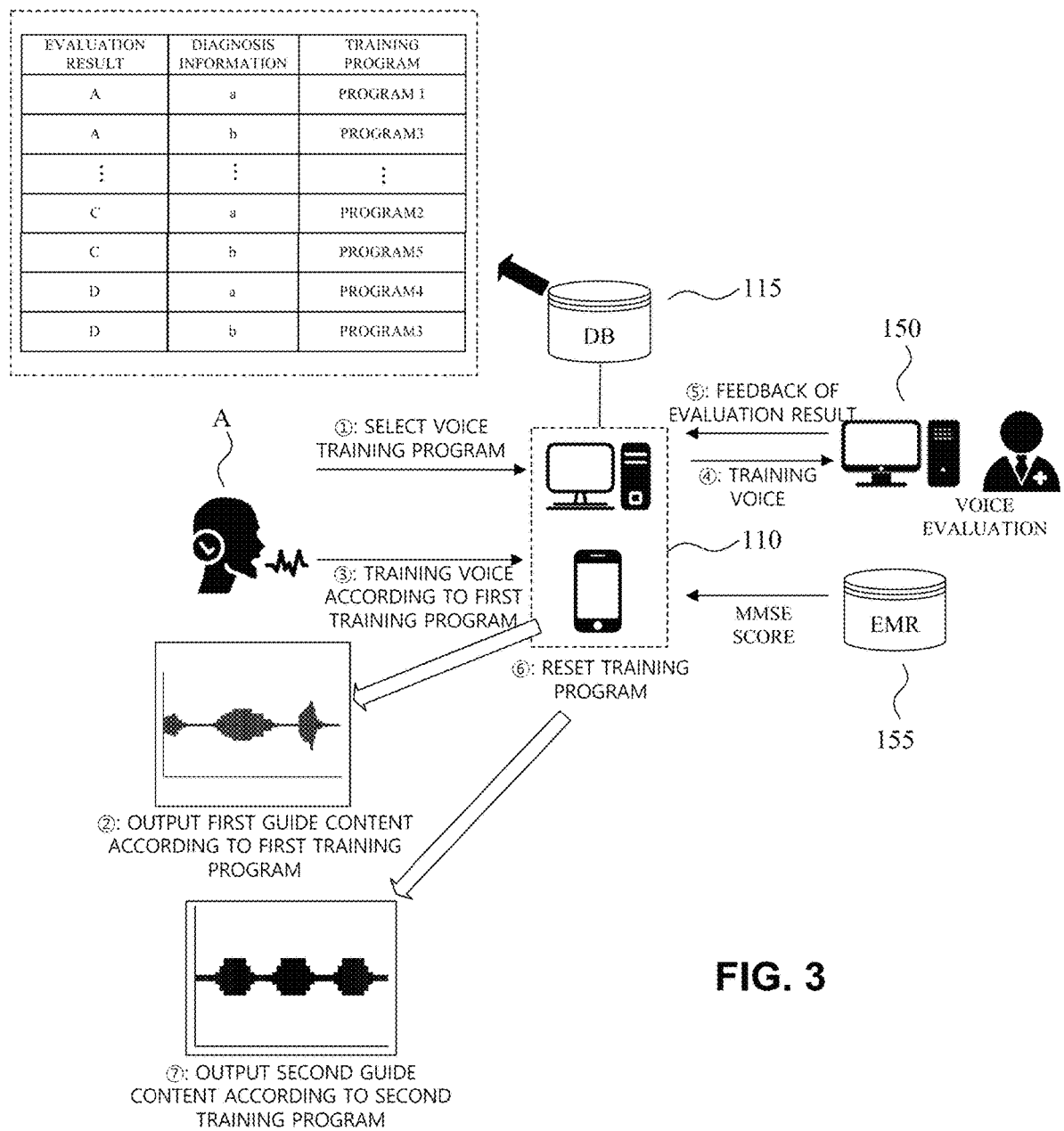
FIG. 3 is a diagram showing an example of a process of providing a voice evaluation of a user and a voice training program.

FIG. 3 is a diagram showing an example of a process of providing a voice evaluation of a user and a voice training program. FIG. 3 illustrates an example of providing voice training on the basis of the user terminal 110 of FIG. 1.

The user terminal 110 provides a voice training program.

A training DB 115 stores various voice training programs in advance. The voice training programs have different types of training content. A voice training program may have different types of content depending on the types of voice disorders or characteristics of a patient. The training DB 115 may store voice training programs matching the types of patients' disorders. The training DB 115 may store voice training programs matching voice evaluation results and the types of disorders. The training DB 115 may store voice training programs matching voice evaluation results and diagnosis information. FIG. 3 shows an example of the training DB 115 storing voice evaluation results, diagnosis information, and voice training programs matching the voice evaluation results and diagnosis information. A matching table may store criteria (at least one of types of disorders, voice evaluation results, and diagnosis information) for defining characteristics of patients, and voice training programs for treating disorders based on the criteria. The criteria and the voice training programs matching the criteria may be determined in advance by medical staff.

A user A performs self voice training using the user terminal 110. First, the user A may select a voice training program to be used in voice training (①). The user A may select a voice training program on the basis of training information provided by the user terminal 110. Alternatively, the user A may select a default voice training program. The selected voice training program is assumed to be a first voice training program. The first voice training program may be a program for collecting samples for voice evaluation. For example, the first voice training program may be a program for vocalizing simple vowels ("A," "I," "U," "E," and "O") for two to three seconds at a constant pitch and strength.

The user terminal 110 outputs first guide content on the screen according to the first voice training program (②). The user terminal 110 receives training voice output according to the first guide content from the user A (③).

As described above, the user terminal 110 may evaluate the training voice itself using an embedded evaluation model. Alternatively, the user terminal 110 may transmit the training voice to the evaluator terminal 150 (④).

The evaluator terminal 150 may evaluate the training voice using an embedded evaluation model. Alternatively, the evaluator terminal 150 may output the training voice and receive an evaluation score based on a certain indicator from an evaluator.

The evaluator terminal 150 transmits the evaluation result of the training voice to the user terminal 110 (⑤).

The user terminal 110 may select a training program matching the evaluation result from the training DB 115. Meanwhile, the user terminal 110 may receive diagnosis information (an MMSE score or the like) of the user A from an EMR server 155. In this case, the user terminal 110 may select a training program matching the evaluation and the diagnosis information from the training DB 115. The user terminal 110 sets the selected voice training program as a second voice training program (⑥).

The user terminal 110 outputs second guide content on the screen according to the second voice training program (⑦). The user A performs voice training according to the second guide content.

The user A may repeat voice training according to the method illustrated in FIG. 3. In this way, the user A may perform voice training optimal to his or her current state. For example, when the voice disorder is improved, the user A is provided with a voice training program reflecting the improvement.

A technique of evaluating user voice will be briefly described. The evaluation technique may be any one of grade, roughness, breathiness, asthenia, and strain (GR-BAS), vocal profile analysis (VPA), and consensus auditory perceptual evaluation (CAPE-V). Among the techniques, GRBAS will be described as an example.

GRBAS includes five evaluation items: grade (G), roughness (R), breathiness (B), strain (S), and asthenia (A). Evaluations are scored in four levels as 0, 1, 2, and 3. Here, 0 is a normal state, and 3 is a state of the worst sound quality. The user A may vocalize a simple vowel, such as "A," "I," "U," "E," or "O," for two seconds at a constant pitch and strength, and the training voice may be evaluated.

The roughness (R) represents a sound caused by irregular vocal cord vibrations and may be a rough sound or unpleasant sound. This sound has an irregular basic frequency or amplitude due to irregular vocal cord vibrations and has noise in a low frequency band. The breathiness (B) represents the light sound of air leaking due to glottic insufficiency and is a noise in the band of a middle or lower register. The asthenia (A) represents a feeble sound with a weak impression caused by vocal cord dystonia. It includes a noise component in a high register, and a fundamental frequency or amplitude smoothly decreases and vocalization ends. The strain (S) represents a sound produced with excessive force when vocal cords are in an abnormally hypertonic state or excessively hard. This sound has a high fundamental frequency, and there is an increase in noise and harmonic components in a high register. The grade (G) represents an overall impression of hoarseness obtained by taking the above items together.

The evaluator may give a GRBAS score for the training voice of the user A. Further, the user terminal 110, the evaluator terminal 150 or 250, or the service server 220 may evaluate the training voice using an evaluation model built in advance. As described above, each item of GRBAS may be evaluated on the basis of frequency-specific features.

Therefore, the evaluation model may convert the input training voice into a frequency band and calculate a GRBAS score on the basis of the converted training voice.

The user terminal 110 or the service server 220 may select a voice training program for the user A according to the evaluation result.

(1) An asthenia (A) score may be the highest for an elderly patient who has a feeble voice and thus has difficulty delivering his or her utterances. In this case, the user terminal 110 or the service server 220 may modify the voice training program to increase voice strength and provide the modified voice training program. Also, the user terminal 110 or 210 may provide information on voice of the user A so that voice strength may be personally checked on the screen.

(2) A roughness (R) score may be high for a patient who has a hoarse voice due to vocal cord paralysis after a stroke. In this case, the user terminal 110 or the service server 220 may provide the voice training program so that the user A may reduce irregularity of sound waves made by him or her and output regular voice. Also, when the user A vocalizes with irregular sound waves, the user terminal 110 or 210 may visually display the irregular sound waves on the screen as feedback.

Guide content output on the screen by the user terminal 110 or 210 according to a voice training program will be described below.

Figure 4:
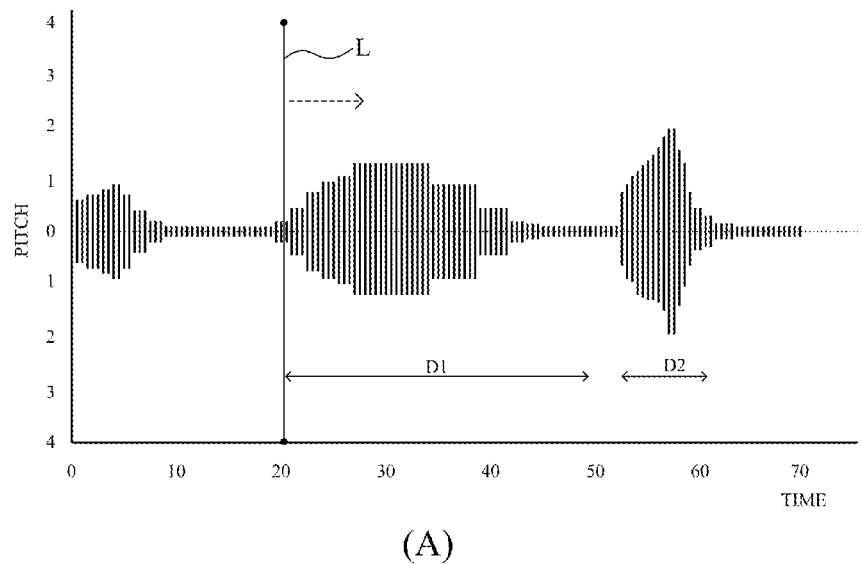
FIG. 4 is a set of graphs showing an example of guide content for a voice training program.
Figure 4:
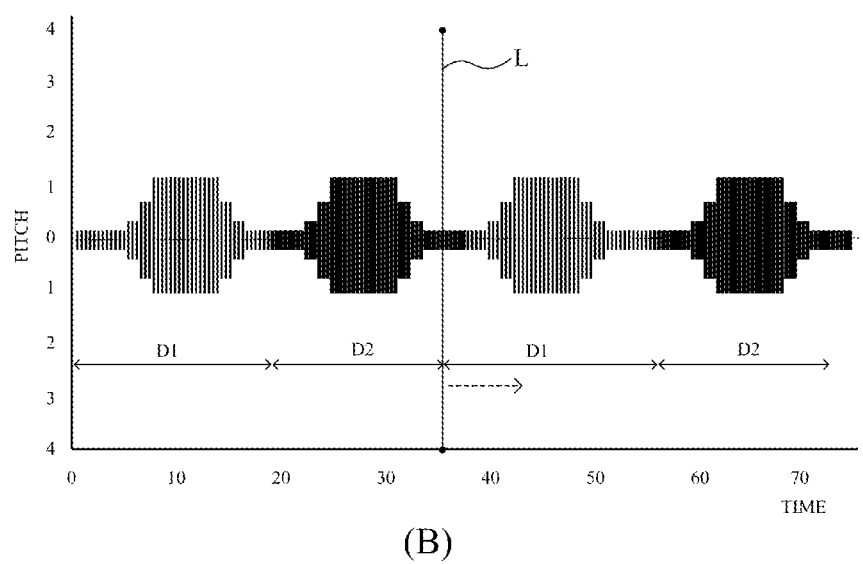

FIG. 4 is a set of graphs showing an example of guide content for a voice training program. FIG. 4 is an example in which a user's utterance sound is expressed in a certain form of wavelengths.

In FIG. 4, the horizontal axis corresponds to time. The numbers on the horizontal axis may be seconds. In FIG. 4, the vertical axis corresponds to the height of a sound. Here, the height of a sound means pitch. The pitch of a sound may be expressed as a frequency. Guide content may differ from that of FIG. 4. For example, the vertical axis may correspond to the intensity of a sound. The intensity of a sound may be expressed as the amplitude (dB) of sound waves.

FIG. 4A is an example of specific guide content according to a voice training program. In other words, a user may train while watching the guide content displayed on the screen and adjusting his or her voice. A line L represents a part to be vocalized at the current point in time. The line L moves right over time. The guide content expresses the length and pitch of a sound to be vocalized for self-training. The guide content may express the pitch of a sound, a change in the pitch of a sound, vocalization of a certain sound, etc. For example, the pitch of a sound in a section D2 rapidly increases compared to a section D1.

FIG. 4B is an example of specific guide content according to a voice training program. In other words, a user may train while watching the guide content displayed on the screen and adjusting his or her voice. A line L represents a part to be vocalized at the current point in time. The line L moves right over time. The guide content expresses the length and pitch of a sound to be vocalized for self-training. Also, the intensity of a sound may be expressed with contrast or thickness of a visual object representing the shape of a sound wave. For example, a visual object in a section D2 is expressed darker than a visual object in a section D1, which means that the user is required to vocalize with higher strength in the section D2 than in the section D1.

In FIG. 4, guide content may express the vocalization period of a sound, the pitch of a sound, a change in the pitch of a sound (a slow change, a rapid change, no change, etc.), a direction of a change in the pitch of a sound (a direction toward a low sound or a direction toward a high sound), the intensity of a sound, etc. In FIG. 4, guide content is a waveform object of voice. The waveform object may represent the length and the pitch or strength of a vocal utterance with the length and height of a waveform, respectively. Alternatively, the waveform object may represent the pitch or intensity of a sound with features (contrast, thickness, etc.) thereof expressing a waveform.

Figure 5:
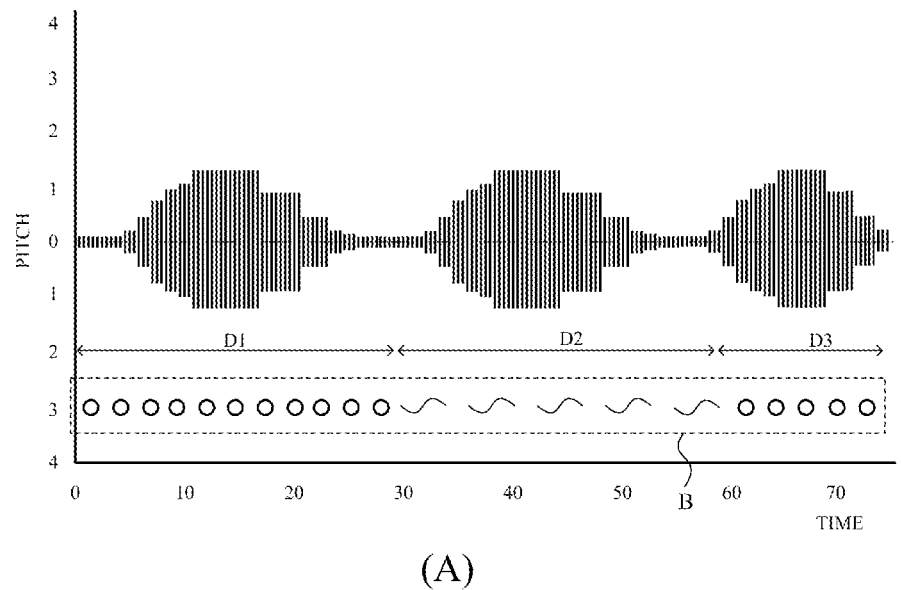
FIG. 5 is a set of graphs showing another example of guide content for a voice training program.
Figure 5:
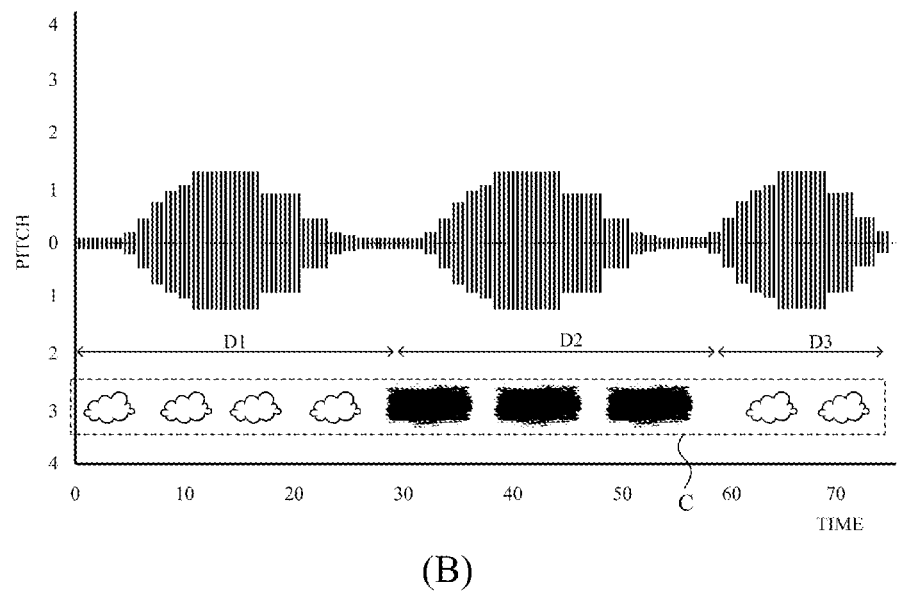

FIG. 5 is a set of graphs showing another example of guide content for a voice training program. FIG. 5 shows guide content having waveform objects like FIG. 4. In FIG. 5, additional information is output on the screen.

FIG. 5A is an example of guide content which additionally provides a sound vocalization method. Additional information is displayed in an area B of FIG. 5A. In a section D1, small circles are displayed. The small circles are staccato signs for dividing vocalization into short and detached sounds. In a section D2, wave shapes are displayed. The wave shapes are legato signs for extending vocalization of a sound for a while. A method of vocalizing a sound or an object representing the method may differ from that in FIG. 5A.

FIG. 5B is another example of guide content which additionally provides a sound vocalization method. Additional information is displayed in an area C of FIG. 5B. Information displayed in the area C represents the intensity of a sound or a slightly abstract vocalization method. In a section D1, cloud objects are displayed. The cloud objects may represent a method of vocalizing a soft or weak sound. In a section D2, objects expressed in a canvas or scratched objects are displayed. The objects in the section D2 may represent a method of vocalizing a strong sound. A method of vocalizing a sound or an object representing the method may differ from that in FIG. 5B.

In FIG. 5, guide content may express the vocalization period of a sound, the pitch of a sound, a change in the pitch of a sound (a slow change, a rapid change, no change, etc.), a direction of a change in the pitch of a sound (a direction toward a low sound or a direction toward a high sound), the intensity of a sound, etc. Further, the guide content of FIG. 5 may provide additional vocalization methods.

Figure 6:
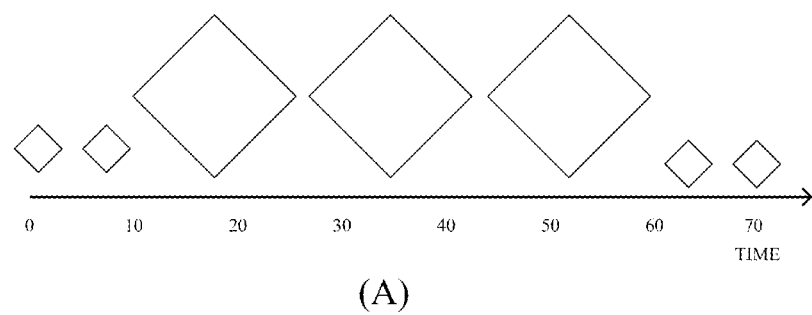
FIG. 6 is a set of graphs showing still another example of guide content for a voice training program.
Figure 6:
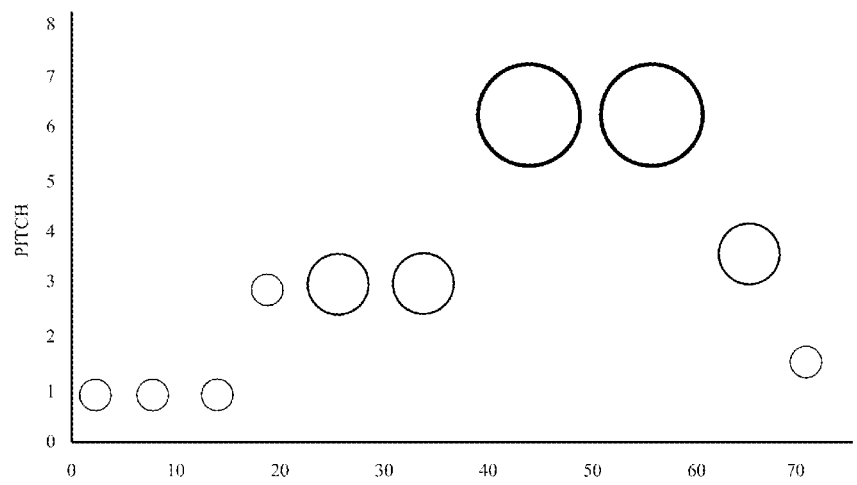

FIG. 6 is a set of graphs showing still another example of guide content for a voice training program. FIG. 6 shows examples of guide content in which waveform objects are different known visual objects. The visual objects may be figures, characters, etc. The characters may be animals, people, or visual objects appearing in animations or the like. FIG. 6 shows certain figure objects. However, guide content may employ figure objects different from those of FIG. 6 or employ character objects instead of figure objects.

In FIG. 6A, the horizontal axis corresponds to time. The numbers on the horizontal axis may be seconds. FIG. 6A shows diamond-shaped objects. The size of a diamond-shaped object may represent the pitch or intensity of a sound. A user may train while watching the guide content displayed on the screen and adjusting his or her voice. The guide content may express a period in which a sound is output and the pitch or intensity of a sound.

In FIG. 6B, the horizontal axis corresponds to time. The vertical axis may correspond to the pitch of a sound. FIG. 6B shows circular objects. A position of a circular object on the vertical axis represents the pitch of a sound. The size of a circular object may represent the intensity of a sound. A user may train while watching the guide content displayed on the screen and adjusting his or her voice. The guide content may express a period in which a sound is output and the pitch or intensity of a sound.

The guide content of FIG. 6 may also display additional information on the screen like in FIG. 5.

In FIG. 6, guide content may express the vocalization period of a sound, the pitch of a sound, a change in the pitch of a sound (a slow change, a rapid change, no change, etc.), a direction of a change in the pitch of a sound (a direction toward a low sound or a direction toward a high sound), the intensity of a sound, etc. In FIG. 6, guide content is a figure object of voice. The figure object may represent the length and the pitch or strength of a vocal utterance with the position and size of a figure, respectively. Further, guide content may represent the intensity of a sound or other information with features (contrast, thickness, etc.) of a figure object.

Figure 7:
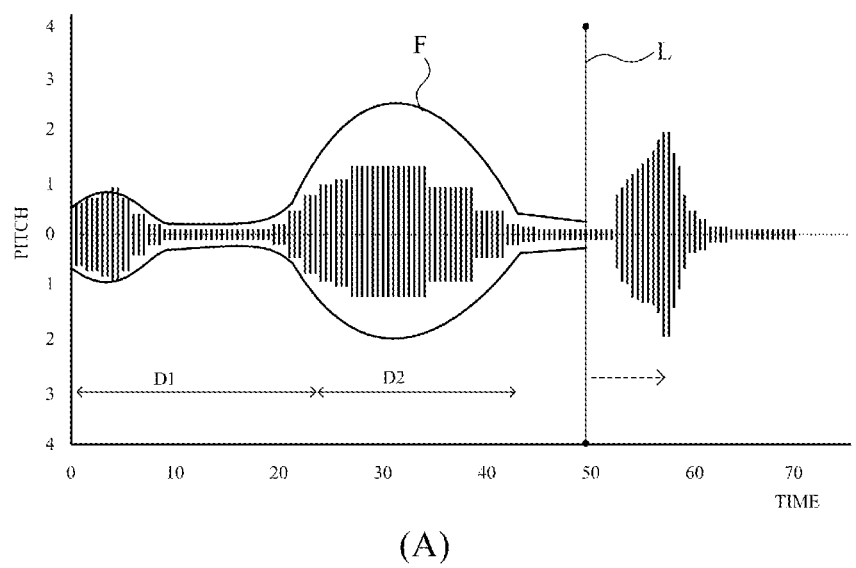
FIG. 7 is a set of graphs showing an example of feedback of a voice training program about a user output.
Figure 7:
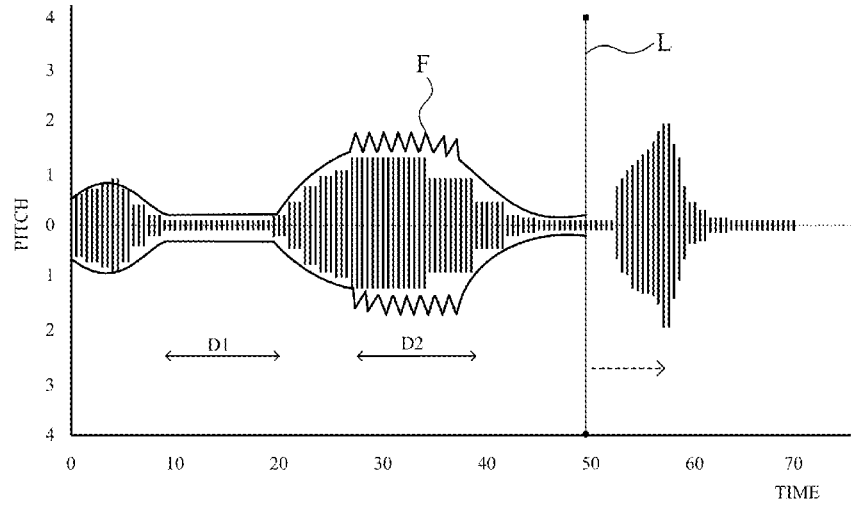

FIG. 7 is a set of graphs showing an example of feedback of a voice training program about a user output. FIG. 7 is a set of examples of displaying information on voice actually produced by a user on a screen which outputs guide content. The user may train while watching the information on the voice actually produced by him or her and adjusting his or her voice at the current point in time. In FIG. 7, the horizontal axis corresponds to time. The numbers on the horizontal axis may be seconds. In FIG. 7, the vertical axis may correspond to the pitch of a sound.

FIG. 7A is an example of specific guide content according to a voice training program. In other words, a user may train while watching the guide content displayed on the screen and adjusting his or her voice. A line L represents a part to be vocalized at the current point in time. The line L moves right over time. The guide content expresses the length and pitch of a sound to be vocalized for self-training.

In FIG. 7A, voice output by the user is expressed as a waveform F. A visual object of voice output by a user is referred to as a feedback object. In a section D1, a waveform object which is the guide content is almost the same as a feedback object. In a section D2, the feedback object is output as a larger value than the waveform object. Accordingly, when looking at the feedback object in the section D2, the user may find that his or her voice is a higher sound than what he or she intends. Subsequently, the user may train while adjusting his or her voice to a slightly lower sound.

In FIG. 7B, voice output by the user is expressed as a waveform F. FIG. 7B is an example of a case in which the user's voice is irregular. In a section D1, a feedback object is expressed as a straight line, which represents that the user outputs a stable sound. In a section D2, the feedback object has a sawtooth shape. The sawtooth shape represents that the user outputs an irregular sound. Accordingly, when looking at the feedback object in the section D2, the user may find that his or her voice is an irregular sound which is not what he or she intends. Subsequently, the user may train while stabilizing his or her voice as much as possible.

A feedback object different from that of FIG. 7 may also be used. For example, when the user vocalizes an irregular sound, the user terminal may output a shaking object.

Figure 8:
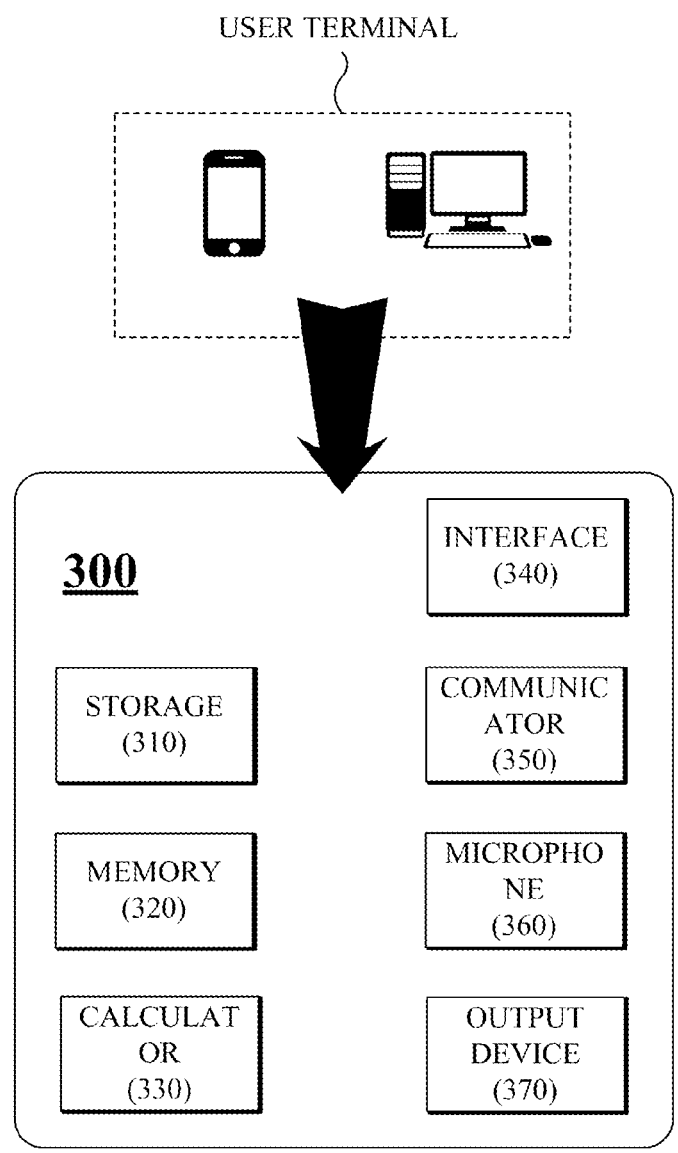
FIG. 8 is a diagram showing an example of a user terminal.

FIG. 8 is a diagram showing an example of a user terminal 300. The user terminal 300 of FIG. 8 corresponds to the user terminals 110 and 210 of FIGS. 1 and 2. The user terminal 300 may be implemented in various forms such as a smart device, a PC, a wearable device, etc.

The user terminal 300 may include a storage 310, a memory 320, a calculator 330, an interface 340, a communicator 350, a microphone 360, and an output device 370.

The storage 310 stores voice training candidate programs for a user's voice training. The storage 310 may be a device embedded in the user terminal 300. Alternatively, the storage 310 may be a separate storage medium that is connected to the user terminal 300 by wire or wirelessly.

A voice training program may be defined by time and at least two elements among the length of an utterance section, the length of an utterance-unit section, the pitch of a sound, a change in the pitch of a sound, the period of time in which the pitch of a sound changes, the intensity of a sound, a change in the intensity of a sound, and the period of time in which the intensity of a sound changes.

The storage 310 may store the user's training voice.

The storage 310 may store an evaluation model for evaluating the training voice.

The storage 310 may store evaluation results of the training voice.

The memory 320 may store temporary data generated in a process in which the user terminal 300 provides guide content according to a voice training program.

The interface 340 is a device to which certain instructions or information is input by the user. The interface 340 may receive certain instructions or data from an external input device. The interface 340 may receive the user's instruction to select a voice training program.

The communicator 350 is a component that receives and transmits certain information through a network. The communicator 350 may transmit training voice to an external object such as an evaluator terminal. Also, the communicator 350 may receive evaluation results of training voice. The communicator 350 may receive diagnosis information (an MMSE score or the like) of the user from an external object such as an EMR server.

The communicator 350 and the interface 340 are devices that externally receive certain data or instructions. The communicator 350 and the interface 340 may also be referred to as input devices.

The calculator 330 selects a specific voice training program from among the voice training candidate programs according to the user's selection and generates guide content according to the selected voice training program.

The calculator 330 may select a specific voice training program from among the voice training candidate programs on the basis of the evaluation result of the training voice and generate guide content according to the selected voice training program.

The calculator 330 may select a specific voice training program from among the voice training candidate programs on the basis of the evaluation result of the training voice and diagnosis information of the user and generate guide content according to the selected voice training program.

The calculator 330 may be a processor, an application processor (AP), or a device for processing data and certain calculations, such as a chip in which a program is embedded.

The microphone 360 receives the user's voice. The microphone 360 receives training voice produced by the user while he or she watches the guide content.

The output device 370 may output an interface screen required for a self-training process. The output device 370 outputs guide content according the voice training program. The output device 370 may output a feedback object for the user's voice.

The output device 370 may output description of the voice training program.

Also, the self voice training method and the operation method of a user terminal described above may be implemented as a program (or application) including an algorithm executable by a computer. The program may be stored and provided in a transitory or non-transitory computer-readable medium.

The non-transitory computer-readable medium is not a medium that stores data for a short period of time, such as a register, a cache, a memory, etc., but a medium that stores data semi-permanently and is readable by a device. Specifically, the above-described various applications or programs may be stored and provided in a non-transitory computer-readable medium such as a compact disc (CD), a digital versatile disc (DVD), a hard disk, a Blu-ray disc, a Universal Serial Bus (USB) memory, a memory card, a read-only memory (ROM), a programmable ROM (PROM), an erasable PROM (EPROM), an electrically erasable PROM (EEPROM), a flash memory, etc.

The transitory computer-readable medium is one of various random-access memories (RAMs) such as a static RAM (SRAM), a dynamic RAM (DRAM), a synchronous DRAM (SDRAM), a double data rate (DDR) SDRAM, an enhanced SDRAM (ESDRAM), a synchronous-link DRAM (SLDRAM), or a direct Rambus RAM (DRRAM).

The above-described technology enables a patient to easily do self-training through a user terminal. The foregoing technology enables even an elderly patient to easily discover his or her own vocalization state (vocalization intensity, a change in vocalization, etc.) using a visual object.

The present embodiments and the drawings accompanying this specification are merely for the purpose of clearly showing some of the technical spirit of the foregoing technology. It will be apparent that all modified examples and specific embodiments that can be easily inferred by those of ordinary skill in the art within the scope of the technical idea included in the specification and drawings of the foregoing technology fall within the scope of the foregoing technology.

What is claimed is:

1. A self voice training method for a patient with a voice disorder, the self voice training method comprising:
   outputting, by a user terminal, first guide content according to a first voice training program of voice training candidate programs for voice training on a screen;
   receiving, by the user terminal, voice output by a user according to the first guide content;
   analyzing and evaluating, by the user terminal using a deep learning model, frequency-specific features of the voice in a frequency band to generate an evaluation result for the first guide content;
   identifying a second voice training program of the voice training candidate programs based on the evaluation result;
   outputting, by the user terminal, second guide content from the second voice training program according to the evaluation result; and
   receiving, by the user terminal, voice output by the user according to the second guide content,
   wherein the first guide content of the first voice training program and the second guide content of the second voice training program are data for outputting content as a visual object over time.

2. The self voice training method of claim 1, wherein the visual object is a waveform object of voice, which represents a length and a pitch or strength of a vocal utterance with a length and height of a waveform, respectively.

3. The self voice training method of claim 1, wherein the visual object is a graphics object, which represents a length and a pitch or strength of a vocal utterance with a relative position of the graphics object based on a specific position and a size of the graphics object, respectively.

4. The self voice training method of claim 1, wherein a voice training program of the voice training candidate programs is defined by a length of an utterance section, a length of an utterance-unit section, a pitch of a sound, a change in a pitch of a sound, a period of time in which a pitch of a sound changes, an intensity of a sound, a change in an intensity of a sound, and a period of time in which an intensity of a sound changes.

5. The self voice training method of claim 1, further comprising outputting, by the user terminal, a graphics object representing a length, a pitch, and a strength of voice and stability of a vocal utterance output by the user according to the first guide content or the second guide content on a screen.

6. The self voice training method of claim 1, wherein the user terminal calculates the evaluation result of the evaluation according to any one evaluation criterion among grade, roughness, breathiness, asthenia, and strain (GRBAS), vocal profile analysis (VPA), and consensus auditory perceptual evaluation (CAPE-V).

7. A self voice training method for a user with a voice disorder, the self voice training method comprising:
   outputting, by a user terminal, first guide content according to a first voice training program of voice training candidate programs for voice training on a screen;
   receiving, by the user terminal, voice output by the user according to the first guide content;
   receiving, from a remote database, diagnosis information regarding a medical state of the user;
   calculating, by the user terminal, an evaluation result using a deep learning model of the voice from a diagnoser terminal based on frequency-specific features of the voice output and the diagnosis information;
   identifying a second voice training program of the voice training candidate programs based on the evaluation result;
   outputting, by the user terminal, second guide content according to the evaluation result on the screen; and
   receiving, by the user terminal, voice output by the user according to the second guide content from the second voice training program,
   wherein the first guide content of the first voice training program and the second guide content of the second voice training program are data for outputting content as a visual object over time, and
   the voice training candidate programs are defined by a length of consecutive utterance sections, a length of an utterance-unit section, a pitch of a sound, a change in a pitch of a sound, a period of time in which a pitch of a sound changes, an intensity of a sound, a change in an intensity of a sound, and a period of time in which an intensity of a sound changes.

8. The self voice training method of claim 7, wherein the visual object is a waveform object of voice, which represents a length and a pitch or strength of a vocal utterance with a length and height of a waveform, respectively.

9. The self voice training method of claim 7, wherein the visual object is a graphics object, which represents a length and a pitch or strength of a vocal utterance with a relative position of the graphics object based on a specific position and a size of the graphics object, respectively.

10. A user terminal for self voice training, the user terminal comprising:
    an input device configured to receive a training program selection command of a user;
    a storage configured to store voice training candidate programs for the user's voice training;
    a calculator, using a deep learning model, configured to generate first guide content according to a first voice training program selected from among the voice training candidate programs by the user;

an output device configured to output the first guide content; and a microphone configured to receive voice output by the user according to the first guide content output through the output device, wherein the calculator selects a second voice training program from among the voice training candidate programs according to an evaluation result of the voice of the user and generates second guide content according to the second voice training program, and the output device outputs the second guide content, wherein the evaluation result of the first guide content output is based on frequency-specific features of the voice output, and the first guide content and the second guide content are data for outputting content of a voice training program as a visual object over time.

11. The user terminal of claim 10, wherein the visual object is a waveform object of voice, which represents a length and a pitch or strength of a vocal utterance with a length and height of a waveform, respectively.

12. The user terminal of claim 10, wherein the visual object is a graphics object, which represents a length and a pitch or strength of a vocal utterance with a relative position of the graphics object based on a specific position and a size of the graphics object, respectively.

13. The user terminal of claim 10, wherein the voice training program is defined by a length of an utterance section, a length of an utterance-unit section, a pitch of a sound, a change in a pitch of a sound, a period of time in which a pitch of a sound changes, an intensity of a sound, a change in an intensity of a sound, and a period of time in which an intensity of a sound changes.

14. The user terminal of claim 10, wherein the output device outputs a graphics object representing a length, a pitch, and a strength of voice and stability of a vocal utterance output by the user according to the first guide content or the second guide content on a screen.

15. The user terminal of claim 10, wherein the evaluation result is based on any one evaluation criterion among grade, roughness, breathiness, asthenia, and strain (GRBAS), vocal profile analysis (VPA), and consensus auditory perceptual evaluation (CAPE-V).

* * * * *